United States Patent [19]
Endencia et al.

[11] Patent Number: 6,130,084
[45] Date of Patent: Oct. 10, 2000

[54] NUTRITION FROM POLLUTION

[76] Inventors: Alex Apolinar C. Endencia, 686 Northwood Dr., Merced, Calif. 95348-2545; Norberto C. Endencia, Tayabas, Quezon, Philippines

[21] Appl. No.: 09/374,966

[22] Filed: Aug. 16, 1999

[51] Int. Cl.[7] .................................................. C12M 1/22
[52] U.S. Cl. .................................... 435/305.1; 435/307.1; 435/308.1; 119/6.5; 119/6.6
[58] Field of Search ................. 119/6.5, 6.6; 435/307.1, 435/308.1, 305.1

[56] References Cited

U.S. PATENT DOCUMENTS 4,849,216  7/1989  Andersen .................................. 424/84

OTHER PUBLICATIONS

Harris, C.R. et al. Outdoor Rearing Technique for Mass Production of Onion Maggots (Diptera: Anthomyiidae), Journal of Economic Entomology 77:824–827, 1984.

Whistlecraft, J.W. et al. Mass Rearing Technique for *Aleochara bilineata* (Coleoptera: Staphylinidae). Journal of Economic Entomology 78:995–997, 1985.

Mish, F.C., editor. Merriam–Webster's Collegiate Dictionary, Tenth Edition. Merriam–Webster, Inc., Springfield, Massachusetts, p. 699, 1997.

The Circle of Life: Daily Living at http://www.fi.edu/tfi/units/life/liviing/living.html. 1999.

Chiou, Y.Y. et al. Production of Maggot Protein Reared on Swine Manure. National Science Council Monthly 10(8):677–682, see Abstract, 1982.

*Primary Examiner*—Karen M. Hauda
*Attorney, Agent, or Firm*—John D. Gugliotta

[57] ABSTRACT

This invention is a trap to collect worms or fly larvae to be used as feed or fowl. Putrid meat is placed inside a a box on top of a metal screen. It is desired to have flies be attracted to the putrid meat and lay their eggs on it. Underneath the meat on top of the screens, warm, wet humus or newspaper is placed and serves as nourishment for the worms when they are hatched. When the larvae are feeding, the screen can be removed in a way to keep the larvae on top and serve as feed for poultry.

11 Claims, 6 Drawing Sheets

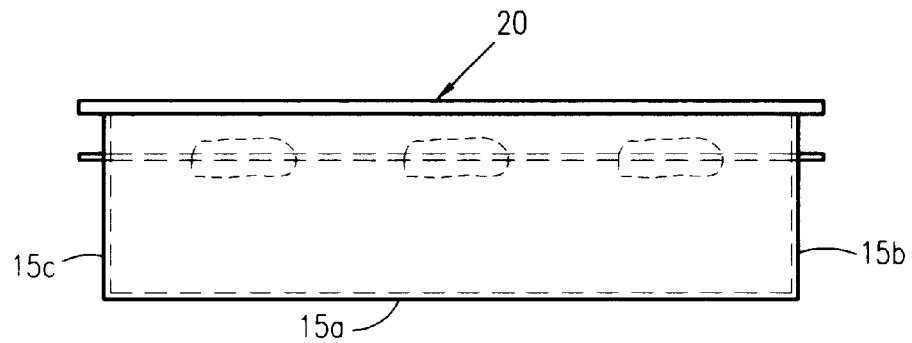
*Figure 3*
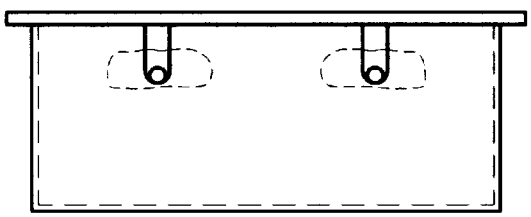
*Figure 4*
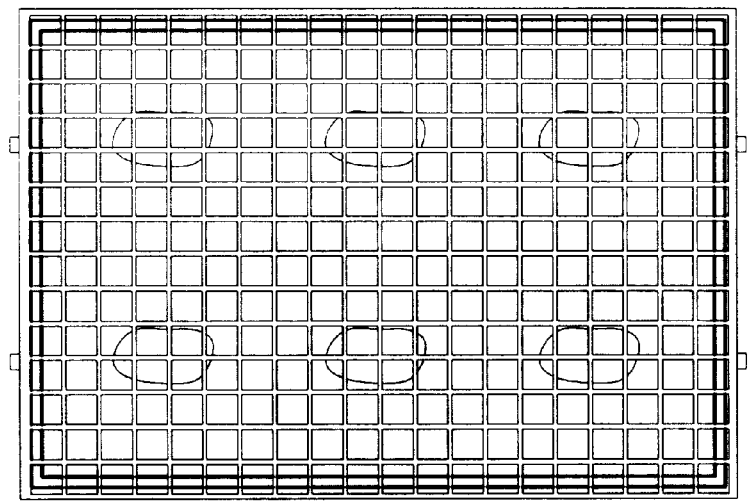
*Figure 5*
*Figure 6*

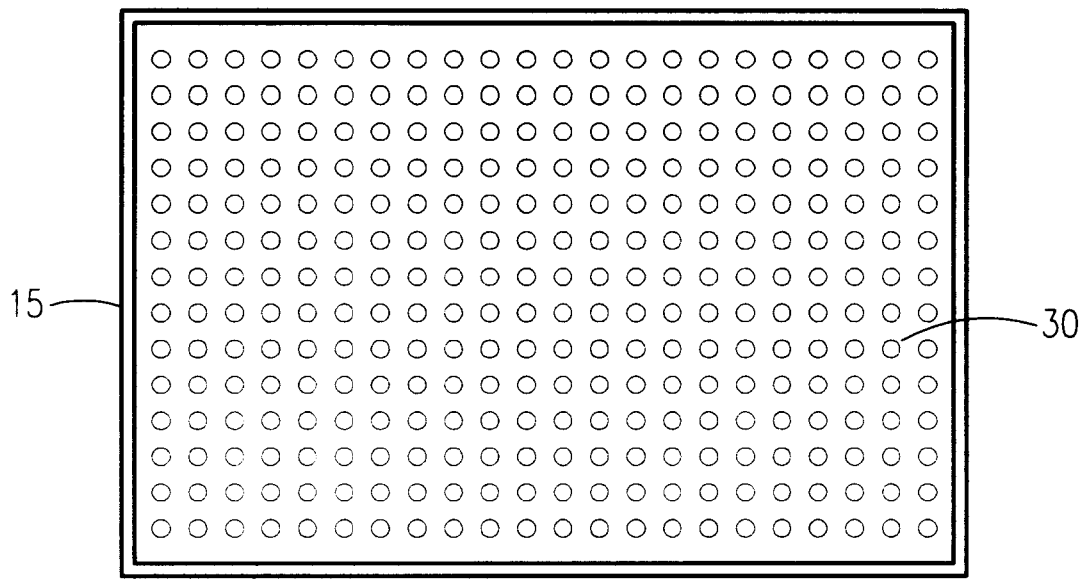
_Figure 9_
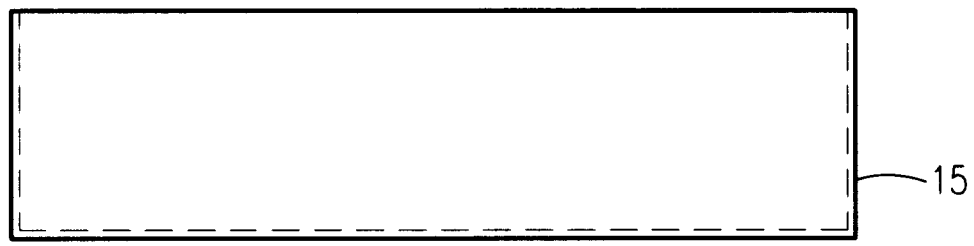
_Figure 10_
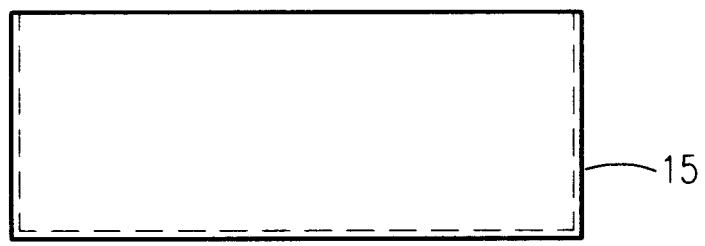
_Figure 11_

NUTRITION FROM POLLUTION

RELATED APPLICATIONS

The present invention was first described in Disclosure Document Number 452500 filed on Mar. 5, 1999. There are no previously filed, nor currently any co-pending applications, anywhere in the world.

BACKGROUND OF THE INVENTION

1. Field of the Invention

The present invention relates generally to a method and apparatus for the production of worms and, more particularly, to a method and apparatus for developing maggot worms from fly larvae for use as feed for poultry.

2. Description of the Related Art

Society's increasing environmental awareness has resulted in a great deal of balancing the cause-and-effect impacts related to such controversial issues as the depletion of the world's forests, air quality, overpopulation, famine and the like in relation to the general impact of mankind on nature and vice-versa. One item that finds a common thread in many of these issues is that of adequate food. Food and its associated nutritional value are important to everyone. Mankind, being at the top of the food chain, often bears the negative impact of environmental and political issues that range from weather issues, food shortages, price increases, local availability and the like. One food that aids in this matter is fowl due to its ready availability and universal acceptance. Chicken, turkey and other such birds are consumed world wide. However, with fowl being relatively high up on the food chain, many of the issues affecting mankind also affect fowl. The price of grain and other food is dependent on the same issues listed above that effect mankind. Thus, a price increase in grain will result in a higher price for the corresponding chicken or other fowl. Another disadvantage with feeding grain to fowl is that the fowl has a harder time digesting the grain and receives less nutritional value from it than compared with worms.

In the related art, various devices and methods have been developed for growing worms and sifting the soil and other mixtures to efficiently and cost effectively harvest the worms. Most of these patents deal with growing earthworms for fishing, waste disposal, processed animal feeds, and fish feeds. However, only one reference, U.S. Pat. No. 4,262,633 issued to Taboga, discloses a means and method whereby earthworms are grown and harvested specifically for feed to poultry. However, such a system requires a much more complex growing and harvesting means because of the larger size of the earthworm as compared to maggots. Growing earthworms requires much more bedding and the means to extract them from soil is even more complex than that of the present invention for maggots. Also, growing earthworms requires that a stock worm population be sorted from an accretion every so often so that a successive generation of earthworms can be produced. The present invention has no such requirement since the maggots are continuously supplied by the larvae flies deposit on the device.

Accordingly, there is a continual need to improve the means by which fowl such as chicken and other fowl are fed to produce food for mankind. The development of the Nutrition from Pollution fowl feeding system fulfills this need.

A search of the prior art did not disclose any patents that read directly on the claims of the instant invention. However, the following references were considered related:

| U.S. Pat. No. | Inventor | Issue Date |
| --- | --- | --- |
| 4,187,946 | Stevenson | February 12, 1980 |
| 4,147,256 | Kiss | April 3, 1979 |
| 4,122,001 | Snyder | October 24, 1978 |
| 4,114,762 | Beal et al. | Sep. 19, 1978 |
| 3,763,593 | Guthrie | October 9, 1973 |
| 1,932,237 | Warner | Sep. 5, 1931 |
| 4,513,685 | Frijters et al. | April 30, 1985 |
| 4,262,633 | Taboga | April 21, 1981 |
| 4,241,532 | Fancy | December 30, 1980 |
| 3,937,354 | Schommer | August 10, 1976 |

SUMMARY OF THE INVENTION

It is an object of the present invention to provide an improved source of nutrition for poultry.

It is another object of the present invention to provide an improved source of nutrition for poultry at little or no cost It is a feature of the present invention to utilize putrid meat, a normally wasted product, as bait for the flies.

It is another feature of the present invention to reduces reliance on outside factors such as weather and politics.

It is yet another feature of the present invention to provide a self contained unit.

It is still yet another feature of the present invention to require low maintenance.

It is yet still another feature of the present invention to provide live feed or dehydrated feed for fowls.

Briefly described according to one embodiment of the present invention, the Nutrition from Pollution fowl feeding system, as its name implies, is a system and method by which worms are farmed as feed for fowl such as chickens or turkey. The use of worms is envisioned to provide a more suitable diet for the fowl as well as reduce dependency on grain and its associated cost. The invention consists of a general box structure, a layered system of wire and metal trays, wet newspaper, and meat in varying stages of decay. The use of the decaying meat attracts flies which lay eggs. The eggs hatch and inhabit the wet newspaper layer. As the worms develop and reach the necessary size, they are harvested, stored or dehydrated for use as feed for domesticated fowl such as chicken or turkeys. With the use of the Nutrition from Pollution fowl feeding system, food for fowl is obtained for basically free, thus reducing the total cost of the fowl, making it an even more attractive food alternative for humans.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

FIG. 3 is a side view of a Nutrition from Pollution worm feeding and harvesting unit, according to the preferred embodiment of the present invention;

FIG. 4. is a front view of a Nutrition from Pollution worm feeding and harvesting unit, according to the preferred embodiment of the present invention;

FIG. 5. is a top view of a Nutrition from Pollution worm feeding and harvesting unit, according to the preferred embodiment of the present invention;

FIG. 6. is side view of a bait rod from a Nutrition from Pollution worm feeding and harvesting unit, according to the preferred embodiment of the present invention;

FIG. 9 is a top view of a worm feeding tray of a Nutrition from Pollution worm feeding and harvesting unit, according to an alternate preferred embodiment of the present invention;

FIG. 10 is a side view of a Nutrition from Pollution worm feeding and harvesting unit, according to an alternate preferred embodiment of the present invention;

FIG. 11 is a front view of a Nutrition from Pollution worm feeding and harvesting unit, according to an alternate preferred embodiment of the present invention.

LIST OF REFERENCE NUMBERS

| 10  | Nutrition from Pollution Unit | 15e | Left Sidewall |
| --- | --- | --- | --- |
| 15  | Feeding Tray | 15f | Bait Rod Slots |
| 15a | Bottom Wall | 20  | Screen |
| 15b | Front Sidewall | 25  | Bait Rods |
| 15c | Rear Sidewall | 30  | Apertures |
| 15d | Right Sidewall | | |

DESCRIPTION OF THE PREFERRED EMBODIMENTS

The best mode for carrying out the invention is presented in terms of its preferred embodiment, herein depicted within the Figures.

1. Detailed Description of the Figures

Figure 1:
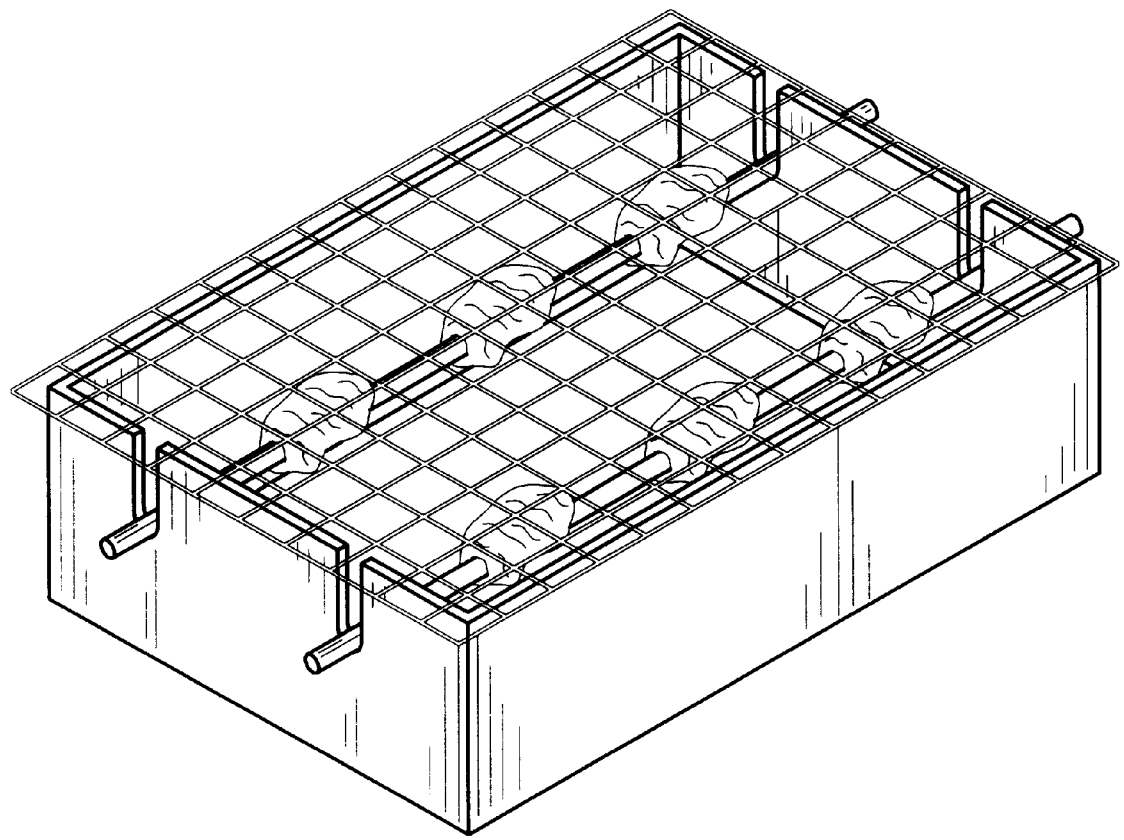
FIG. 1 is a perspective view of a Nutrition from Pollution worm feeding and harvesting unit, according to the preferred embodiment of the present invention.

Referring now to FIG. 1, shown is a an exploded perspective view of a Nutrition from Pollution worm harvesting and feeding unit, according to the preferred embodiment of the present invention, comprised of a feeding tray 15, screen 20, and a plurality of at least two bait rods 25. Feeding tray 15 is of a generally rectangular shape having a bottom wall 15a, front sidewall 15b, rear sidewall 15c, right sidewall 15d, and left sidewall 15e. The aforementioned walls of feeding tray 15 are formed from thin sheets of material capable of being 20 formed, cut, and fastened together and sufficient rigidity to form a sturdy yet lightweight container capable of being stacked one on top of the other and supporting the weight of the contents therein. Suggested materials would include plastic or conventional stainless steel but any suitable material would be satisfactory as long as it is rust resistant. Cut into the front sidewall 15b and rear sidewalls 15c are a plurality of at least two bait rod slots 15 for receiving one end of a bait rod 25. Bait rod 25 is a slender rod having an elongated longitudinal axis and cut to a length slightly longer than the length of bottom wall 15a. Bait rod 25 must be at least long enough so that each of two ends protrude a short distance past right sidewall 15d and left sidewall 15e when said ends are placed into a bait rods slot 15f in said right sidewall 15d and left sidewall 15e. The two ends of by rods 25 are ground to a sharp point for skewering rancid meat product leftovers much like when one prepares shish kebab for grilling. It is envisioned that at least two such bait rods 25 would be utilized with each feeding tray 15. This requires that two bait rods slots 15f be provided for each bait rod 25 with one bait rod slot 15f formed in each of said front sidewall 15b and rear sidewall 15c located directly inapposite each other.

Figure 2:
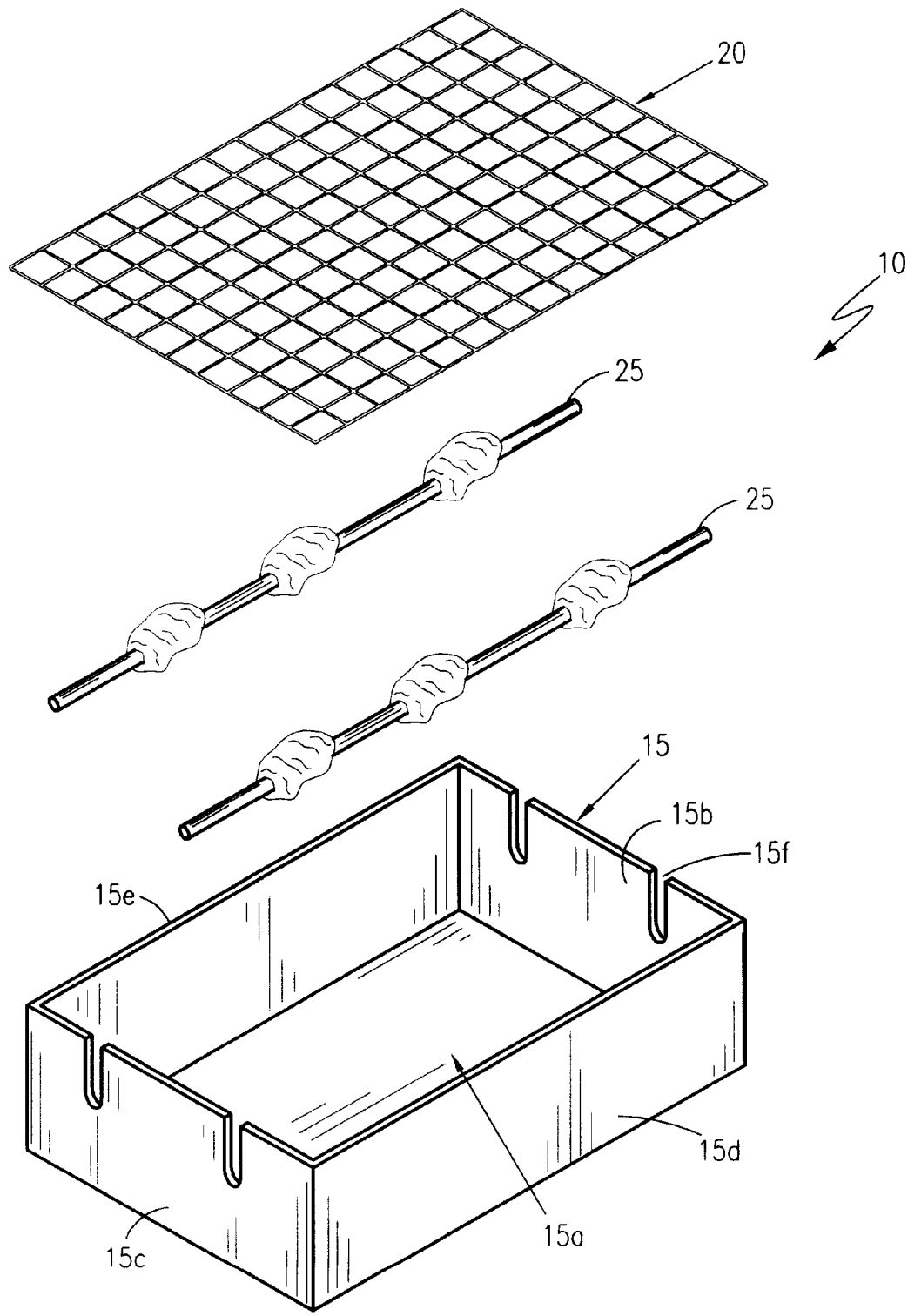
FIG. 2 is an exploded perspective view of a Nutrition from Pollution worm feeding and harvesting unit, according to the preferred embodiment of the present invention.

Referring to FIG. 2, shown is a perspective view of an assembled Nutrition from Pollution worm harvesting and feeding unit, according to the preferred embodiment of the present invention. Screen 20 rests on the upper edges of right sidewall 15d, left sidewall 15e, front sidewall 15b, and rear sidewall 15c. Screen 20 is generally rectangular in shape and just slightly larger than feeding tray 15 so that its edges slightly overlap the upper edges of feeding tray 15. Screen 20 can be made out of any material that conventional screens are manufactured from with the only limitation being that whatever material that is chosen must be rust resistant and somewhat stiff so that when individual Nutrition from Pollution worm harvesting and feeding units are stacked Screen 20 does not buckle. The weave of the mesh be large enough that fly eggs may fall through but small enough that a mature fly cannot pass through.

FIG. 3 shows a side view of feeding tray 15 with one of the bait rods placed into the a bait rod 25 slot 157 formed into front sidewall 15b and rear sidewall 15c. Bait rods 25 require no special means to hold them into place except to rest in bait rod slots 157. Bait rods 25 are place in such a fashion that air is free to circulate around the decaying meat skewered on the rods 25. Located beneath bait rods 25 is an area in which an environment conducive to fly larvae maturation is created. This is accomplished by providing a layer of bedding material on top of bottom wall 15a. This bedding material can consist of old newspapers crumpled or shredded or humus soil. In either case, the beds are kept warm and moist and continuously monitored.

Referring now to FIGS. 4, 5, and 6, of a Nutrition from Pollution worm harvesting and feeding unit, according to the preferred embodiment of the present invention, showing more detail of worm tray 15 in FIGS. 4 and 5, and of bait rod 25 in FIG. 6.

Figure 7:
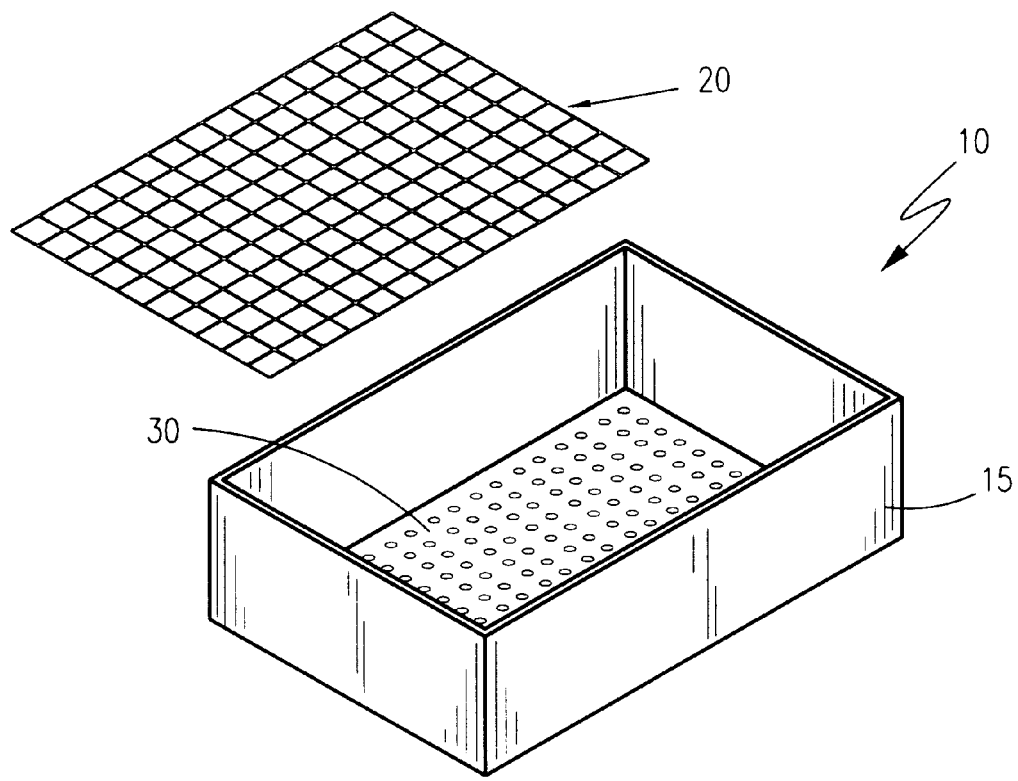
FIG. 7 is an exploded perspective view of a Nutrition from Pollution worm feeding and harvesting unit, according to an alternate preferred embodiment of the present invention.
Figure 8:
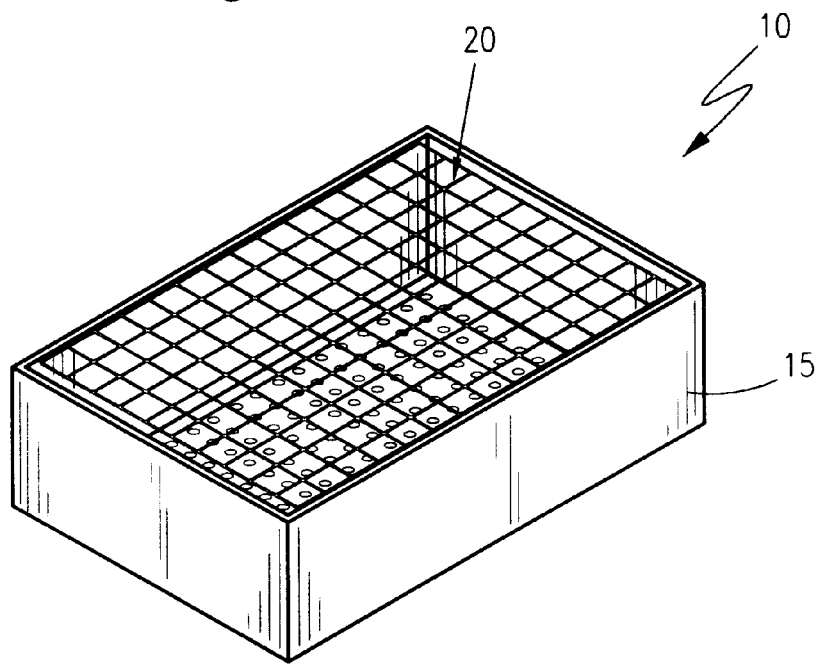
FIG. 8 is a perspective view of a Nutrition from Pollution worm feeding and harvesting unit, according to an alternate preferred embodiment of the present invention.
Figure 12:
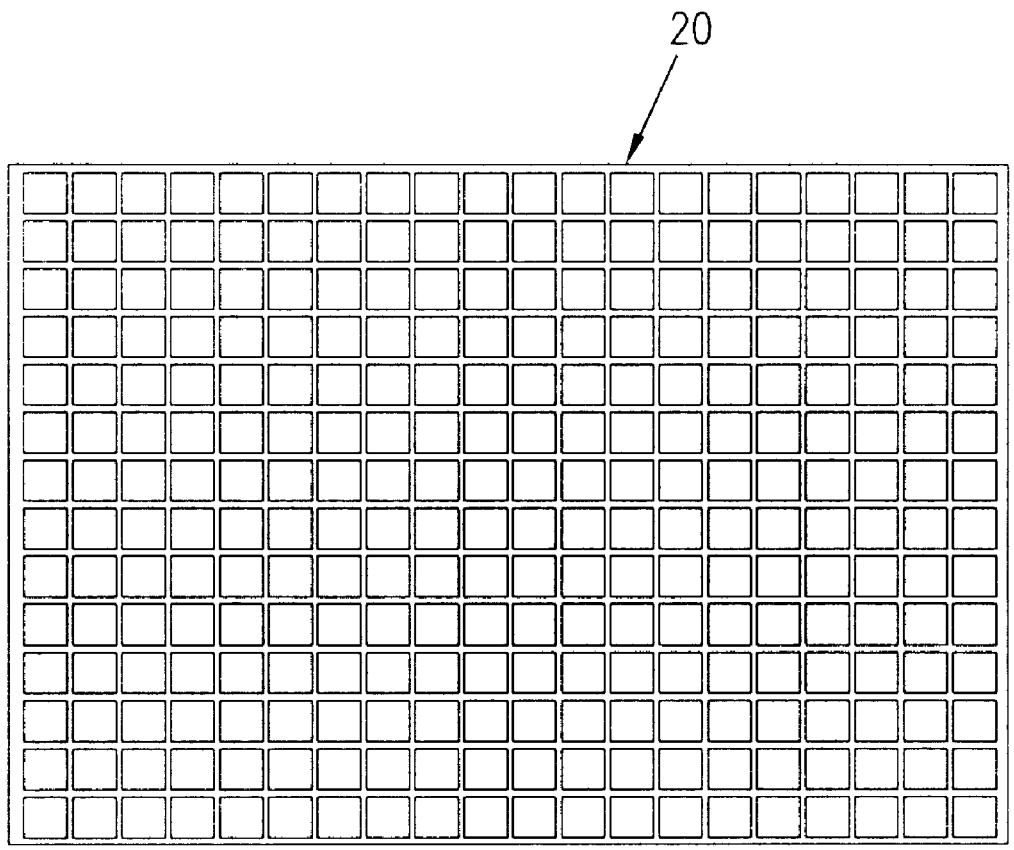
FIG. 12 is a top view of a filtering screen from a Nutrition from Pollution worm feeding and harvesting unit, according to an alternate preferred embodiment of the present invention.

Referring now to FIG. 7, shown is a an exploded perspective view of a Nutrition from Pollution worm harvesting and feeding unit, according an alternate preferred embodiment of the present invention, comprised of a feeding tray 15, screen 20, and a plurality of apertures 30 formed in the bottom wall 1 5a of feeding tray 15. Feeding tray 15 and screen 20 are constructed as previously described except that screen 20 is now slightly smaller than feeding tray 15 to fit inside thereof and a plurality of small apertures are now formed in bottom wall 15a of feeding tray 15 organized in rows and columns. Apertures 30 allow excess moisture to drain from feeding tray 15 and to allow circulation of air in the bedding located therein. The bait rods 25 and bait rod slots 15f are eliminated. Meat waste is laid directly now on the bedding and flies are free to lay their eggs directly on the bedding. When the larvae mature into maggot worms, screen 20 is lifted and the worms sifted from the bedding. The slightly larger maggot worms are too big to fall through the mesh of screen 20. The worms are then collected and used as feed for poultry.

Referring now to FIGS. 8 through 12, shown are various views of a Nutrition from Pollution worm harvesting and feeding unit, according to an alternate preferred embodiment of the present invention.

2. Operation of the Preferred Embodiment

In operation, it is envisioned that to collect sufficient numbers of fly larvae and to breed the maggot worms for a commercially viable operation would require that many of the previously described Nutrition from Pollution worm harvesting and feeding units 10 would be necessary. These could possibly number in the hundreds and would require a suitable shelter to house them. The shelter would have to be open to the environment to allow mature flies to enter the shelter to lay their eggs. Since many of the units would be required to produce sufficient numbers of worms it would be necessary to stack the units on top of each other and a rack system could be built for this purpose. Of course, a supply of water, newspaper, humus soil, a source of waste meat products, and a climate where flies are present year round is also necessary.

To use the units, crumpled or shredded newspaper or humus soil is placed into feeding tray and then moistened. Chunks of meat waste are then skewered onto the bait rods. The bait rods are then placed across feeding tray 15 with the ends placed into the specially formed bait rod receiving slots. The screen is then placed over the feeding tray. The units are then left with the meat decaying. The smell of the decaying meat will attract flies who will try to get at the meat. However, the screen will prevent them from doing so. In all likeliness, the fly, in their eagerness to get at the meat, will drop their eggs onto the screen. The mesh of the screen is specially designed to be large enough to allow the eggs to fall through and onto the bedding below. The warm, moist bedding is a perfect environment to allow the eggs to mature into maggot worms. It is essential that the units are checked often to see if the eggs has matured into the desired maggot worms. Once this has happened, the worms can be removed from the bedding by shaking them from the newspaper or sifting the humus soil through a sifter. The worms are then collected and sent to a poultry plant where they are fed to poultry. The worms may also be dehydrated to prevent them from further maturing into flies so that they can be stored or sent to poultry plants further away from the worm production facility.

In an alternate preferred embodiment, instead of placing the screen on the top of the feeding tray, a slightly smaller screen is laid on the bottom of the feeding tray before the humus or newspaper is put into it. The bait rods are eliminated and the meat waste is put directly on top of a bedding of moist humus soil. The flies are then free to lay their eggs directly on the bedding. When the eggs mature into maggot worms the screen is lifted and the humus is allowed to fall through the mesh while the maggot worms remain of the screen. Small apertures in the bottom wall of the feeding tray are provided for ventilation to the bedding and to allow excess moisture to drain off. The mature maggot worms are then processed as described above.

The foregoing description is included to illustrate the operation of the preferred embodiment and is not meant to limit the scope of the invention. The scope of the invention is to be limited only by the following claims.

What is claimed is:

1. An apparatus for the production and harvesting of maggot worms, consisting of:
    a feeding tray, said feeding tray being of a generally rectangular shape and having a bottom wall, front sidewall, rear sidewall, right sidewall, and left sidewall;
    a screen, said screen being generally rectangular in shape and just slightly larger than said feeding tray so that its edges slightly overlap the upper edges of feeding tray and wherein said screen rests on an upper edge of said right sidewall, said left sidewall, said front sidewall, and said rear sidewall;
    a plurality of at least two bait rod slots, said bait rod slots formed in said front sidewall and said rear sidewall for receiving one end of a bait rod;
    a plurality of at least two bait rods, wherein said bait rods are a slender rod having an elongated longitudinal axis and cut to a length slightly longer than the length of said bottom wall and at least long enough so that each of two ends protrude a short distance past said right sidewall and said left sidewall when said ends are placed into said bait rod slots formed in said front sidewall and said rear sidewall.

2. The apparatus for the production and harvesting of maggot worms of claim 1, wherein said bottom wall, front sidewall, rear sidewall, right sidewall, and left sidewall are formed from thin sheets of material capable of being formed, cut, and fastened together and of sufficient rigidity to form a sturdy yet lightweight container capable of being stacked one on top of the other and supporting the weight of the contents therein.

3. The apparatus for the production and harvesting of maggot worms of claim 2, wherein said material is selected from the group comprising plastic or conventional stainless steel.

4. The apparatus for the production and harvesting of maggot worms of claim 3, wherein said the ends of said bait rods are ground to a sharp point for skewering rancid meat product leftovers much like when one prepares shish kebab for grilling.

5. The apparatus for the production and harvesting of maggot worms of claim 4, wherein at least two bait rods would be utilized with each said feeding tray which requires that two of said bait rods slots be provided for each said bait rod, one of said bait rod slots being formed in said right sidewall and in said left sidewall located directly opposite each other.

6. The apparatus for the production and harvesting of maggot worms of claim 5, wherein said screen can be made out of any material that conventional screens are manufactured from with the only limitation being that whatever material that is chosen must be rust resistant and somewhat stiff to prevent buckling and the weave of the mesh be large enough that fly eggs may fall through but small enough that a mature fly cannot pass through.

7. The apparatus for the production and harvesting of maggot worms of claim 6, wherein:
    said bait rods are placed in such a fashion that air is free to circulate around the the rancid meat product leftovers on said bait rods;
    a layer of bedding material is provided on top of said bottom wall and located beneath said bait rods to provide an environment conducive to fly larvae maturation; and
    said bedding material consists of materials selected from the group comprising old crumpled or shredded newspapers or humus soil, and wherein said beds are kept warm and moist and continuously monitored.

8. An apparatus for the production and harvesting of maggot worms, consisting of:
- a feeding tray, said feeding tray being of a generally rectangular shape and having a bottom wall, front sidewall, rear sidewall, right sidewall, and left sidewall;
- a screen, said screen slightly smaller than said feeding tray to fit inside thereof; and
- a plurality of apertures, said plurality of apertures formed in said bottom wall of said feeding tray, and further, said apertures being organized in rows and columns to allow excess moisture to drain from said feeding tray and to allow circulation of air in bedding located on top of said screen with said screen placed in said bottomwall.

9. The apparatus for the production and harvesting of maggot worms of claim 8, wherein:
- meat waste is laid directly on said bedding and flies are free to lay larvae directly on said bedding;
- said screen is lifted and the worms sifted from the bedding when the eggs mature into maggot worms because the slightly larger maggot worms are too big to fall through the mesh of said screen.

10. The apparatus for the production and harvesting of maggot worms of claim 7, wherein said maggot worms are collected and used as feed for poultry.

11. The method and apparatus for the production and harvesting of maggot worms of claim 8, wherein said maggot worms are collected and used as feed for poultry.

* * * * *